(12) United States Patent
Oguma

(10) Patent No.: US 6,198,964 B1
(45) Date of Patent: Mar. 6, 2001

(54) BODY FAT MEASURING DEVICE WITH LCD DRIVER HAVING TERMINALS COMMONLY USED FOR SWITCH

(75) Inventor: Koji Oguma, Fujisawa (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/233,029

(22) Filed: Jan. 20, 1999

(30) Foreign Application Priority Data

Jan. 28, 1998 (JP) .................................... 10-029051

(51) Int. Cl.[7] ........................................ A61B 5/05
(52) U.S. Cl. ............................................ 600/547
(58) Field of Search ................................. 600/547

(56) References Cited

U.S. PATENT DOCUMENTS 5,415,176 * 5/1995 Sato et al. ............................ 600/547

* cited by examiner

*Primary Examiner*—William E. Kamm
(74) *Attorney, Agent, or Firm*—Evenson, McKeown, Edwards & Lenahan, P.L.L.C.

(57) ABSTRACT

In a body fat measurement device provided with a LCD and multiple SWs, at least one LCD drive terminal of said LCD driver is connected to said SW directly or indirectly with a current limit element such as a resistor therebetween so as to work as a switchable terminal for either an input or an output, and said terminal is usually set to work as an output terminal for driving said LCD, and is periodically set to work as an input terminal 10 for receiving an input for a certain period negligibly shorter than a LCD drive period by a controller and thereby gets a state of being a SW, and said input is stored into a memory.

7 Claims, 7 Drawing Sheets

BODY FAT MEASURING DEVICE WITH LCD DRIVER HAVING TERMINALS COMMONLY USED FOR SWITCH

BACKGROUND AND SUMMARY OF THE INVENTION

This application claims the priority of Japanese application No. 29051, filed Jan. 28, 1998, the disclosure of which is expressly incorporated by reference herein.

1. Field of the Invention

The present invention relates to a small-sized device, provided with a LCD display and multiple switches (SWs), for measuring body fat percentage.

2. Description of the Prior Art

With the growing desire for health and good body form among people in recent years, the concerns about overweight control tends to shift from weight to body fat percentage. A weight measuring scale provided with a meter for measuring body fat percentage (hereafter referred to as a scale with fat meter) was proposed and is already on the market. A scale with a fat meter, however, is often larger than an ordinary scale, because electrodes and switches are necessary for measuring body fat percentage. A more small-sized scale having a fat meter is desired due to the house size conditions and other reasons. In a scale having a fat meter the space for installing an electronic circuit board is limited because a comparatively large space is occupied by associated mechanical parts such as electrodes, a scale mechanism, etc. for measuring body fat percentage. Further, the area of the circuit board is also limited by respective A/D portions which occupy a comparatively large area for measuring body fat percentage and weight.

A fat meter mainly employs an impedance method. In this method, a bio-impedance of a human body is measured and converted into an amount of fat. Accordingly, values of conversion parameters such as sex, height, age, weight, etc. of a measured person are necessary. Though weight can simultaneously be measured by a scale having a fat meter, other parameters must be input by the measured person. Since it is a nuisance to input these conversion parameters each time to measure body fat percentage, a scale provided with multiple "personal keys" is already on the market.

This scale is very handy because each "personal key" allows each measured person to register his or her own parameters such as sex, height, and age which are constant or do not change within a short period and each measurement can be implemented only by pushing each "personal key". This scale, however, usually demands 4 to 5 "personal keys" besides a key for setting these parameters.

Since a scale having a fat meter, compared with an ordinary scale, tends to display more information and to have more pins for LCD, providing more switches increases the number of control and input devices and the wires for these devices occupy a wider area. Conventionally, a LCD device was connected to a device for the LCD drive and a separate input device was used for a SW because of the problems described below.

The LCD display drive is generally so complicated that an exclusive device is required. Both the LCD display drive and the SW state detection must always be implemented. When a driver for a LCD and an input device for a SW are wired to an identical terminal, an abnormal indication occurs, for example, that a LCD segment not to be lit is lit because the electric potential of the terminal is set to either Hi or Lo depending on the SW state.

Though a control device (micro-controller) having both a LCD driver and an input device integrated is already on the market, the micro-controller must have many pins because both devices separately use respective pins. This naturally causes the micro-controller to be larger, demanding more space for wiring, and eventually makes it difficult to save space.

Though the use of a multi-layer interconnection board usually leads to a small-sized board, this manner allows only the wiring portion to be reduced and on the other hand greatly pushes up the cost of the board. Therefore, it has been difficult to reduce the board size.

The object of the present invention is to provide a means for a smaller and less expensive board for a body fat measuring device which has a LCD and multiple SWs and is constituted so as to allow a common terminal to be used simultaneously for both driving a LCD and inputting the SW state and so as to accomplish a smaller device with less terminals eventually.

According to an aspect of the present invention, there is provided a body fat measuring device comprising a body fat measuring sensor, a controller, a memory, a LCD driver, a LCD, and a SW for setting such personal data as sex, height, etc. for measuring the body fat percentage in a human body. At least one LCD drive terminal of said LCD driver, which works as a switchable terminal for either an input or an output, is connected to said SW directly or indirectly with a current limit element such as a resistor, therebetween. The terminal is usually set to work as an output terminal for driving said LCD. The terminal is periodically set to work as an input terminal for an input for a certain period negligibly shorter than a LCD drive period by the controller and thereby is set as a SW, and the input is stored into said memory.

According to another aspect of the present invention, there is provided a body fat measuring device for measuring the body fat percentage in a human body comprising a body fat measuring sensor, a controller, a memory, a LCD driver, a LCD, and a SW for setting such personal data as sex, height, etc. At least one LCD drive terminal of the LCD driver, which works as a switchable terminal for either an input or an output, is connected to the SW directly or indirectly with a current limit element such as a resistor therebetween. The terminal is usually set to work as an output terminal for driving said LCD. The terminal is periodically set to work as an input terminal for an input for a certain period negligibly shorter than a LCD drive period by the controller. During the certain period all common terminals are set to an intermediate voltage between the minimum and maximum of the driver voltage, and thereby is set as a SW, and said input is stored into said memory.

Other objects, advantages and novel features of the present invention will become apparent from the following detailed description of the invention when considered in conjunction with the accompanying drawings.

BRIEF DESCRIPTION OF THE DRAWINGS

The present invention and its preferred embodiment will be described in greater detail with reference to the accompanying drawings, in which.

DESCRIPTION OF THE PREFERRED EMBODIMENTS

Figure 1:
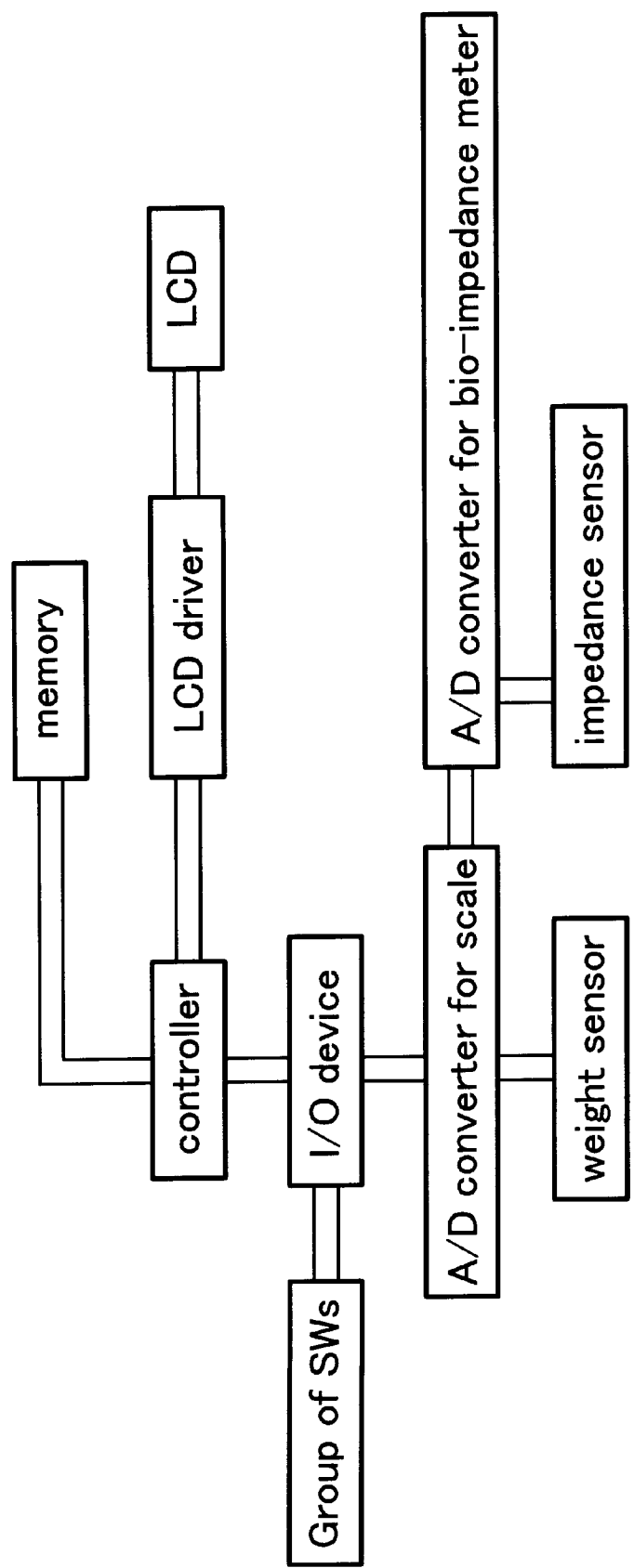
FIG. 1 is a block diagram of the constitution of a scale with fat meter.

Referring to FIG. 1, a scale having a body fat meter mainly comprises a weight sensor, an LCD, an LCD, an A/D converter for a scale, an A/D converter for a bio-impedance meter, an impedance sensor, a controller, a memory, an I/O device and a group of switches.

Figure 2A:
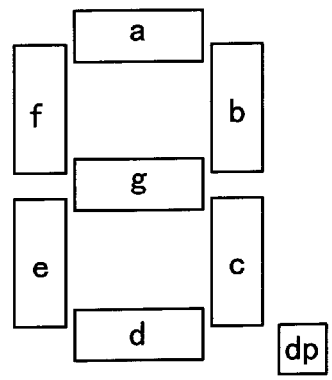
FIG. 2A is a schematic plan view of a dynamically driven LCD according to ½ bias method and 2-time sharing method.
Figure 2B:
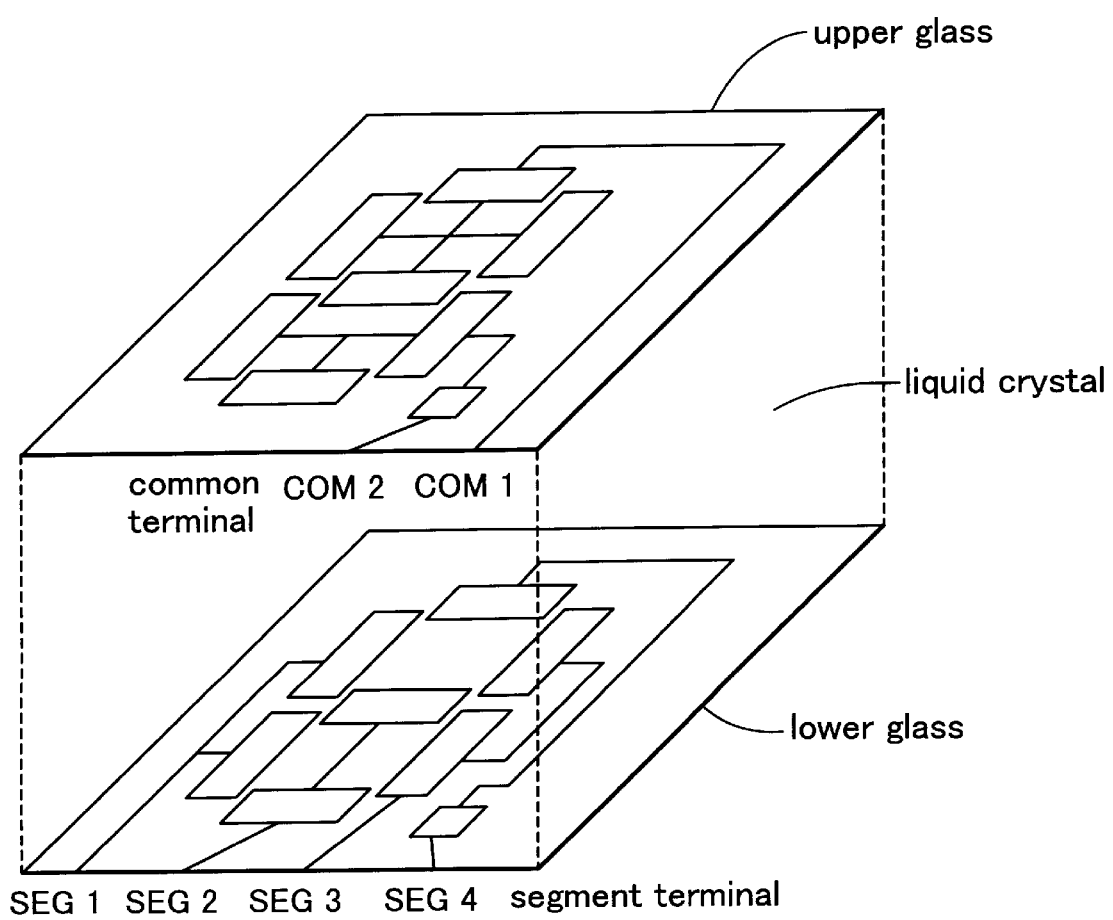
FIG. 2B is a schematic perspective view of the LCD of FIG. 2A.

Referring now to FIGS. 2A and 2B, an LCD provided with multiple segments is usually driven by a method called dynamic drive. A device for dynamic drive comprises a common terminal and a segment terminal, and wires to the segments are arranged in a matrix and each segment is located on the matrix.

As the simplest examples, the half bias method and the 2-time sharing method will be described.

In case of the half bias method, 0V, Vdd, and ½ Vdd which is a half of Vdd, are used for LCD drive.

In case of the 2-time sharing method, one period of the alternating current applied for the LCD drive is divided in two and a voltage to make LCD display effective is applied to each of two common terminals separately for each half period. Each display segment is arranged as a pattern on two sheets 10 of glass constituting a LCD.

As shown in FIGS. 2A and 2B, on one sheet of glass, the segments wired to the common terminals are arranged in two patterns while every two segments wired to a segment terminal is arranged in a pattern on the other sheet of glass. To each segment, wires from common terminals and segment terminals are arranged in a matrix.

In a LCD, each segment is lighted by a liquid crystal located between the glass sheets and polarizing plates disposed below and above the LCD when an alternating voltage higher than a certain level is applied to the segment. Each segment is put out when an alternating voltage higher than a certain level is applied to the segment.

Figure 3:
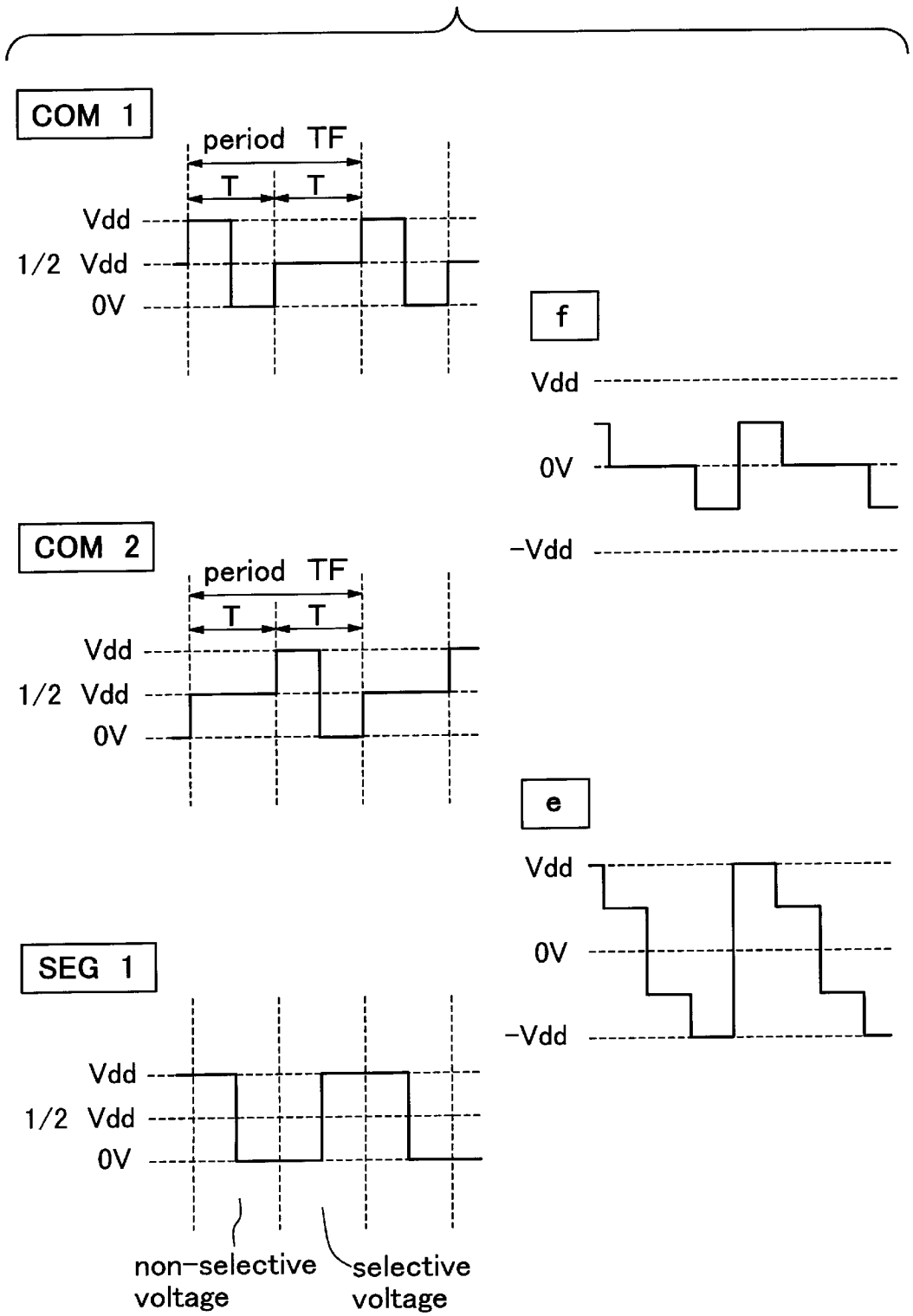
FIG. 3 is a schematic voltage diagram of a dynamically driven LCD according to ½ bias method and 2-time sharing method.

To turn segments "f" and "e" on and off respectively in FIGS. 2A and 2B, a non-selective voltage is applied to SEG1 while an effective voltage is output to COM1. A selective voltage is applied to SEG1 while an effective voltage is output to COM2 because "f" is wired to COM1 and SEG1 and "e" is wired to COM2 and SEG1. Since the voltage applied to segment "f" is the difference between those applied to the terminals SEG1 and COM1, the difference is an alternating voltage with the peaks ±½ Vdd as shown in FIG. 3.

The voltage applied to segment "e" is the difference between those applied to the terminals SEG1 and COM2 and is an alternating voltage with the peaks ±Vdd. Accordingly the segment "f" is not lighted and the segment "e" is lighted by employing a LCD which is designed not to be lighted by an alternating voltage with the peaks ±½ Vdd but is designed to be lighted by an alternating voltage with the peaks ±Vdd.

As seen from the simplest dynamic drive described above, the LCD drive is thus complicated and an exclusive hardware has been necessary.

Figure 4:
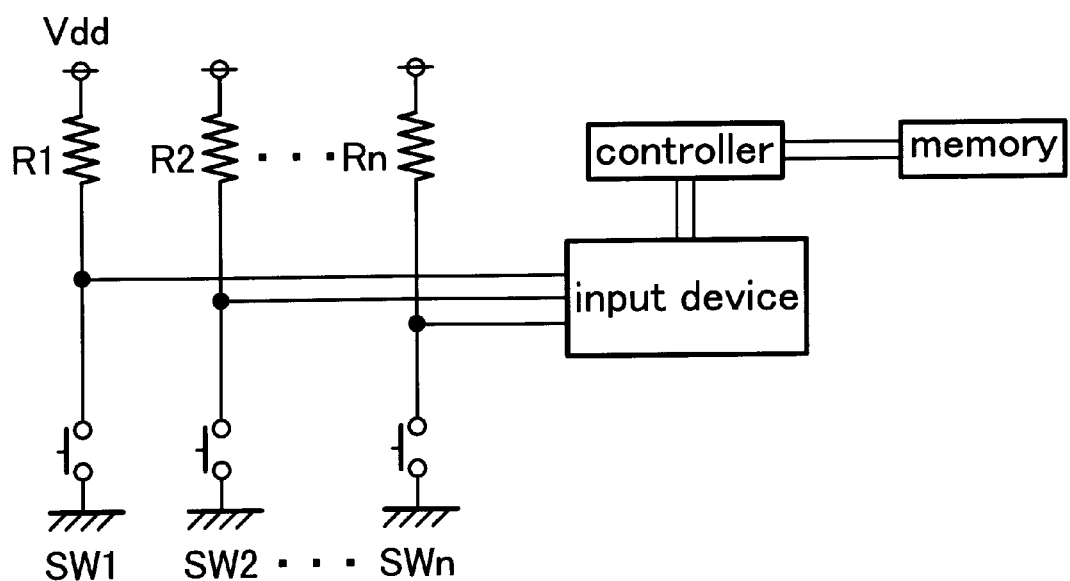
FIG. 4 is a block diagram of a SW portion.

Referring to FIG. 4, how to detect whether a SW is pushed or not will be described below. One end of a SW is grounded to 0V and the other end is connected to both an input device and a resistor. The other end of the resistor is applied with a voltage Vdd. The terminal connected to the input device is set to Lo (0V) when the SW is connected, and is set to Hi (Vdd) when disconnected.

A controller continuously monitors the state of the SW through the input device, and implements various processing after the controller judges that the SW has been pushed (the voltage has changed from Hi to Lo). Since various processing, not restricted to that for the SW, must be implemented by the controller, the state of the switch, i.e., whether the SW is pushed or not, is consecutively detected, for example, every 5 milliseconds.

For detecting the state of each SW, a short time is necessary from several micro seconds to several micro hundred seconds. Taking into account during this short time, according to a basic technical concept of the present invention, (a) A LCD driver is constituted to work as hardware allowing both input and output.

(b) A LCD driver terminal to be used for both input and output is alternately set by a controller so as to detect the state of the SW or driving the LCD at the intervals of a predetermined period.

(c) The period for detecting the state of the SW is made negligibly shorter than that for driving the LCD.

Though an exclusive device is necessary for LCD display drive as described in the above, the driver can work either for driving the LCD display or for detecting the state of a SW when the hardware constitution is changed so as to allow both input and output.

Though both functions of driving the LCD display and detecting the state of the SW are always implemented as described in the above, a device can implement both functions if the device is alternately set either for LCD display drive or the SW state detection by a controller.

Though some disturbance, as described in the above appears in the LCD display due to the SW voltage change from Hi to Lo and vice versa when a common terminal is used, the disturbance can almost be eliminated, i.e., hardly be displayed, because the error in the LCD drive voltage caused by the SW can be made small by making the period for detecting the state of the SW negligibly shorter than that for driving the LCD.

By accomplishing these subjects described above, the LCD drive continues to work almost consecutively and the terminal for detecting the state of the SW can be combined with that for driving the LCD.

According to the present invention, an I/O switching device, controlled by a controller, is provided so that the connection of the I/O device is switched from an output device for LCD drive to an input device for SW detection and vice versa.

A timer is provided to the controller, and the switchable terminal is set to an input terminal for an input device to detect an input with in a short period and then is set to an output terminal for an output device by the I/O switching device at the intervals of a predetermined period. The detected input while the terminal is working as an input terminal is stored into a memory. When the controller (microcomputer) sets the terminal to be a SW, the data stored in the memory is read and the SW state is detected at any time.

Figure 5:
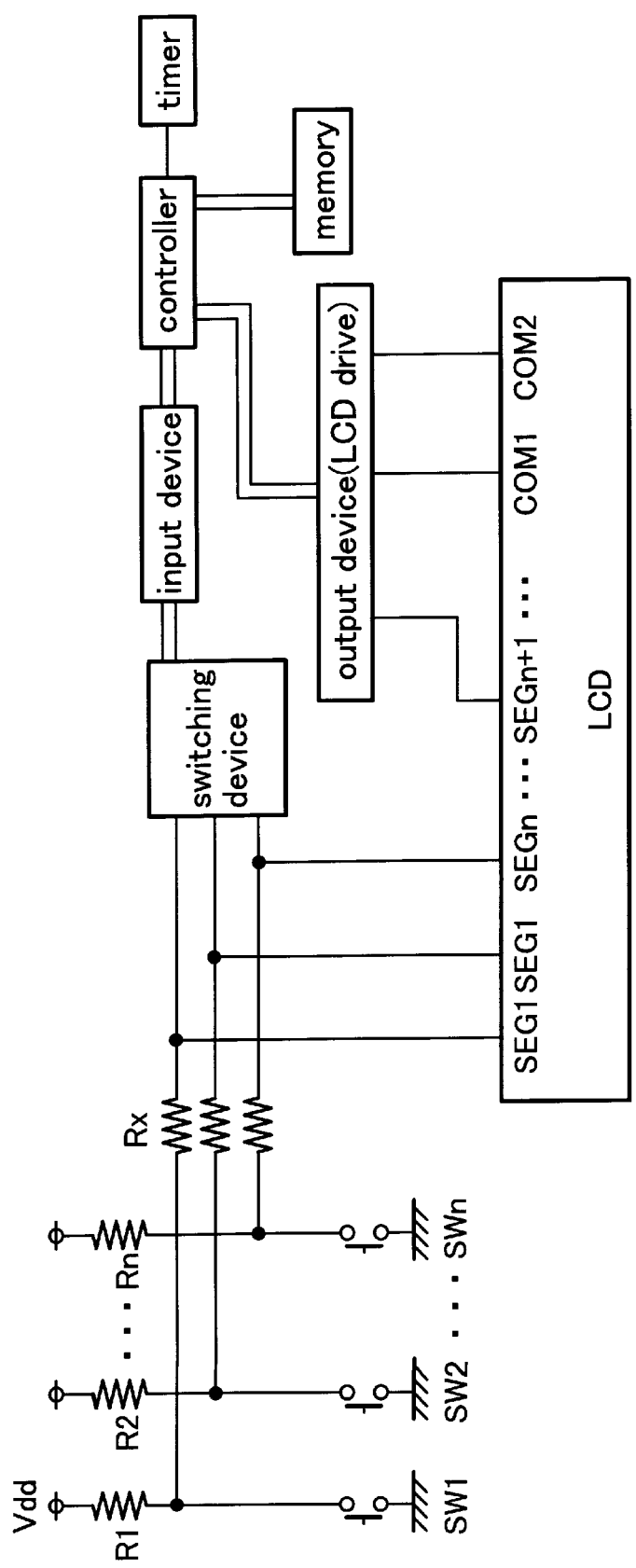
FIG. 5 is a block diagram of main part of an embodiment of the present invention.

FIG. 5 shows an embodiment of the present invention. A group of resistors Rx are provided between respective LCD terminals and respective SWs so as to limit an excessive current. This prevents an excessive current which might flow due to a short circuit if any output except Lo (Hi, etc.) is output during the period that a terminal is switched to an output device (LCR driver) by a controller and a SW is pushed and the terminal is applied with the voltage Lo.

Rx is not always necessary so long as an excessive current can be prevented. For example, when a resistor sufficiently smaller than R1 is provided between a SW and GND (0V) to prevent a short circuit state even if the SW is pushed, Hi can be detected when the SW is disconnected and Lo, which is nearly 0V, can be detected when the SW is pushed.

Figure 6:
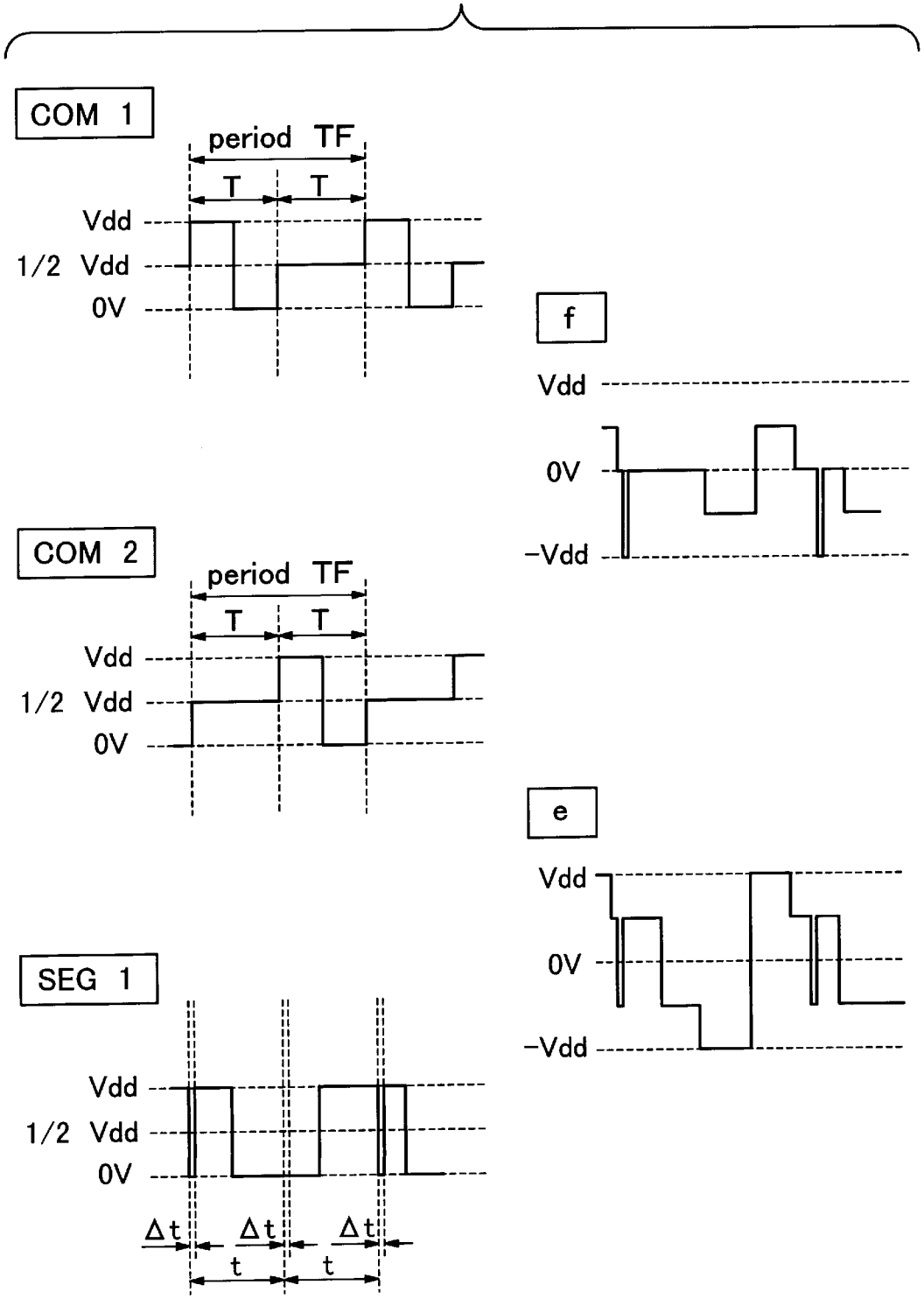
FIG. 6 is a LCD voltage diagram of an embodiment of the present invention.

FIG. 6 shows a waveform of said LCD segment when the controller switches the terminal to the input device for detecting the state of the SW at the intervals of "t". SW1 is assumed to be always pushed, i.e., is kept at Lo. SEG1 and SW1 are connected to each other with a resistor R1 there between.

Therefore, at the intervals of "t" the waveform of SEG1 is set to Lo of SW1 for a very short time, $\Delta t$ that is, during a short period that the terminal is switched to the input device by the controller. Since the period that the terminal is switched to the input device is very short, the disturbance in the segment waveform of LCD due to the effect of Lo applied to the terminal fades out shortly afterward. This means that the present embodiment allows SW state detection with no substantial effect on the LCD display.

Figure 7:
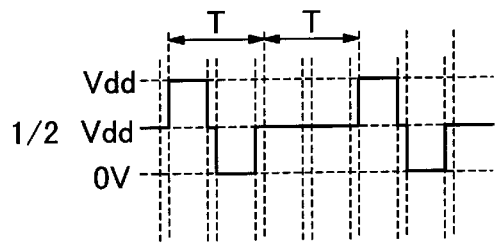
FIG. 7 is a LCD voltage diagram of another embodiment of the present invention.
Figure 7:
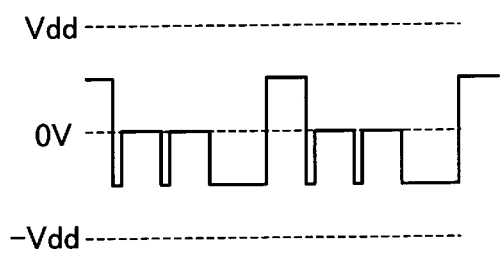
Figure 7:
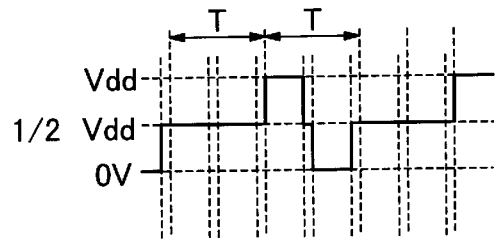
Figure 7:
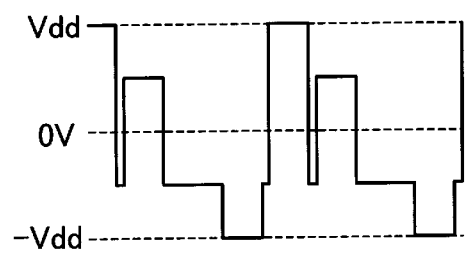
Figure 7:
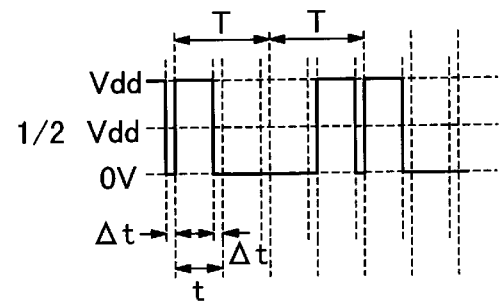

Though the embodiment above is practical enough the voltage "−Vdd", though instantaneously, appears in the waveform of the voltage applied to the segment "f" as shown in FIG. 6. This suggests that the segment "f", which should not to be lighted, might dimly be lighted and thereby might be visible. Therefore, this voltage "−Vdd" must be prevented for a LCD display of higher quality. FIG. 7 shows an example of LCD drive as a means for eliminating this problem.

The controller sets the output device (LCD driver) so that all the common terminals are applied with ½ Vdd during the period that the terminals are switched to the input device for detecting the state of the SW. This means that the voltage applied to each segment, i.e., the difference between the voltages applied to the SEG terminal and the COM terminal, is set to ±½ Vdd regardless of the SW ON/OFF (0V or Vdd) during the period that the SW state is detected. Preferably, the period "t" for switching to the input device is synchronized with the half of the period "T" for switching the voltages applied to the segment/common terminals of LCD. This eliminates a timer for generating "t".

Though "t" is equal to ½ T in the embodiment of the LCD driver of FIG. 7, "t" may be a period which is any multiple of ½ T, for example, ³⁄₂ T.

Since the terminals COM1, COM2 are set to ½ Vdd during the processing period $\Delta t$ for detecting the SW state, the segment is applied with −½ Vdd when the SW is pushed (0V).

Since the terminal SEGM1 is set to Vdd during the period $\Delta t$ that the SW is not pushed, the segment "f" is applied with ½ Vdd. Therefore, the segment "f" is unlighted because it is applied only with a voltage between ±½ Vdd regardless of the SW ON/OFF, and a good LCD display is accomplished without such phenomenon that the segment is dimly lighted.

In a body fat measuring device having many LCD terminals and multiple SWs, the present invention allows not only that the device be made smaller through the drastic reduction in the number of terminals by integrating those terminals, but also allows an IC to be smaller in chip area and less expensive through the least number of required terminals because the chip area of a comparatively simple IC, which performs such function as accomplished by the present device, is mainly restricted by the number of terminals. A smaller board leads to a more inexpensive board. Further the wires for packaging an IC chip and the soldered connections for isolating a board are also reduced, and thereby the poor installation due to them is eventually reduced.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A body fat measuring device for measuring the body fat percentage in a human body comprising a body fat measuring sensor, a controller, a memory, a LCD driver, a LCD, a SW for setting personal data such as sex, height and age, wherein at least one LCD drive terminal of said LCD driver, is operable as a switchable terminal for either an input or an output and, is connected to said SW directly or indirectly with a current limit element therebetween, said terminal being is usually set to operate as an output terminal for driving said LCD, said terminal being periodically set by said controller to work as an input terminal for an input during a certain period negligibly shorter than a LCD drive period and thereby being set as said SW, and said input is stored into said memory.

2. A body fat measuring device according to claim 1, wherein said current limiting device is a resistor.

3. A body fat measuring device according to claim 1, wherein said current limiting device is a plurality of resistors.

4. A body fat measuring device for measuring the body fat percentage in a human body comprising a body fat measuring sensor, a controller, a memory, a LCD driver, a LCD, a SW for setting personal data such as sex, height and age, wherein at least one LCD drive terminal of said LCD driver is operable as a switchable terminal for either an input or an output, and is connected to said SW directly or indirectly with a current limit element therebetween, said terminal being usually set to work as an output terminal for driving said LCD, said terminal being periodically set to operate as an input terminal for an input for a certain period negligibly shorter than a LCD drive period by said controller, further wherein during said certain period all common terminals are set to an intermediate voltage between a minimum and a maximum driver voltage, thereby being set as a SW, and said input is stored into said memory.

5. A body fat measuring device according to claim 4, wherein said current limiting device is a resistor.

6. A body fat measuring device according to claim 4, wherein said current limiting device is a plurality of resistors.

7. A method for measuring body fat percentage comprising the steps of;

arranging a body fat sensor, a controller, a memory, a LCD driver, a LCD, and a SW adapted to set personal data, within a body fat measuring device;

operating at least on LDC terminal of the LCD driver as a switchable terminal for use as an input or an output;

positioning a current limiting element between the terminal and the SW;

setting the terminal to operate primarily as an output terminal for driving the LCD device;

periodically setting the terminal to operate as an input terminal to input data from the SW for a period of time shorter than a period of time during which the terminal is operated to drive the LCD device; and storing the input data in the memory.

* * * * *